United States Patent [19] [11] Patent Number: 4,866,370
Flemming et al. [45] Date of Patent: Sep. 12, 1989

[54] MATERIAL CHARACTERIZATION

[75] Inventors: Michael A. Flemming; Graham N. Plested, both of Oxfordshire, England

[73] Assignee: United Kingdom Atomic Energy Authority, London, United Kingdom

[21] Appl. No.: 294,797

[22] Filed: Jan. 9, 1989

[30] Foreign Application Priority Data

Jan. 22, 1988 [GB] United Kingdom ................. 8801395
Mar. 7, 1988 [GB] United Kingdom ................. 8805364

[51] Int. Cl.$^4$ ..................... G01R 27/26; G01R 27/04
[52] U.S. Cl. ............................. 324/518 C; 324/58.5 C
[58] Field of Search .............. 324/58 C, 58.5 C, 58 R, 324/58.5 R, 57 SS, 57 Q

[56] References Cited

U.S. PATENT DOCUMENTS

| 3,586,971 | 6/1971 | Bosisio | 324/58.5 C |
| 4,270,083 | 5/1981 | Fitzky et al. | 324/58.5 C |
| 4,277,741 | 7/1981 | Faxvog et al. | 324/58.5 C |
| 4,453,125 | 6/1984 | Kimura et al. | 324/58.5 A |

FOREIGN PATENT DOCUMENTS

| 842514 | 6/1981 | U.S.S.R. | 324/58.5 C |
| 715415 | 9/1954 | United Kingdom . | |
| 890412 | 2/1962 | United Kingdom . | |
| 1550062 | 8/1979 | United Kingdom . | |

Primary Examiner—Reinhard J. Eisenzopf
Assistant Examiner—Maura K. Regan
Attorney, Agent, or Firm—William R. Hinds

[57] ABSTRACT

A method of characterizing a material uses an element in which microwaves can propagate and can resonate, such as a weakly-coupled isolated microstrip device or a microwave cavity, arranged so that fringing fields from the element interact with the material. Microwaves are coupled into the element at a frequency near a resonance, and a modulating signal is applied so as to modulate the response of the element. Measurements of both the mean response and the modulation of the response enable the dielectric constant and dielectric loss of the material to be determined. Modulation may be applied to the frequency of the microwaves, or to the electrical parameters of the element.

12 Claims, 2 Drawing Sheets

MATERIAL CHARACTERIZATION

The invention relates to a method for characterising a material by determining at least one electrical property of the material, and to an apparatus for performing the method.

Information about a material may be obtained, as described in UK patent application No. GB 2 202 947 A, by placing a probe incorporating an isolated resonant microstrip element in contact with the material so that fringing fields from any microwaves propagating in the element will interact with the material, coupling microwaves into the element, and sensing the microwaves propagating in the element. If the microwave frequency is scanned through a natural resonant frequency of the element then it will undergo a resonance. The resonant frequency and the sharpness of the resonance (Q) can both be determined, and these two parameters enable the dielectric constant (relative permittivity) and the dielectric loss of the material to be determined. Although this technique does enable the material to be characterised it is expensive because of the requirement for a broad-band variable frequency microwave generator.

According to the present invention there is provided a method for characterising a material, the method using an element in which microwaves can propagate and can resonate, the method comprising arranging the material in such a position relative to the element that at least a part of the electromagnetic fields due to microwaves propagating in the element extend into the material, coupling microwaves into the element at a frequency near to a resonant frequency, sensing the microwave response of the element, both the coupling means and the sensing means being coupled to the element sufficiently weakly to have negligible effect on its natural resonance, and applying a modulating signal so as to modulate the response, hence obtaining a first signal indicative of the mean response, and a second signal indicative of the rate of change of the response with frequency, and using the first and the second signals to characterise the material.

The element might be an isolated resonant microstrip component arranged adjacent to the material, or it might be a resonant chamber within which the material can be placed. The further the frequency is from the resonant frequency, the more difficult is it to characterise the material, because the signals obtained with different materials become more similar. By a frequency near to a resonant frequency is meant a frequency at which the microwave response is significantly affected by the presence of the resonance; typically the power of the response is within about 3 dB of the power at the peak of the resonance, i.e. the power is more than about a half of the power at the peak. The first signal and the second signal might be used to determine both the dielectric constant and the dielectric loss of the material, for example by means of a computerised look-up table. The modulation might be achieved by modulating the frequency of the microwaves; alternatively the modulating signal might vary the natural resonant frequency of the element, which may be achieved by varying the capacitance between two parts of the element for example by applying a modulating signal to a voltage-dependent capacitor (e.g. a varactor diode).

The invention also provides an apparatus for performing the above-described method.

The invention will now be further described, by way of example only, and with reference to the accompanying drawings in which.

Figure 1:
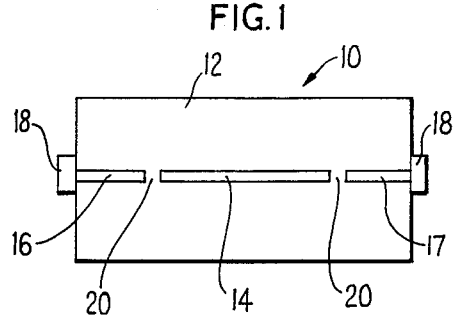
FIG. 1 shows a plan view of a probe for use in the invention.

Referring now to FIG. 1, this shows a probe 10 comprising a thin sheet or substrate 12 of polytetrafluoroethylene/glass fibre laminate, with a thin layer of copper (not shown) on its rear surface, and on its front surface a resonant microstrip element 14 in the form of a straight strip of copper, and input and output microstrips 16 and 17 colinear with the element 14. Each microstrip 14, 16 and 17 is of characteristic impedance 50 ohms. Coaxial cable connectors 18 at each end of the substrate 12 enable microwaves to be coupled into or out of the microstrips 16 and 17, and enable the rear surface copper layer to be earthed. Gaps 20 between the ends of the element 14 and the microstrips 16 and 17 are 1.0 mm wide, providing a coupling capacitance of only about 20 fF and so ensuring that if the probe 10 is connected to a source and a detector of microwaves, the microstrip element 14 is not significantly loaded by the impedances of the source or of the detector.

Figure 2:
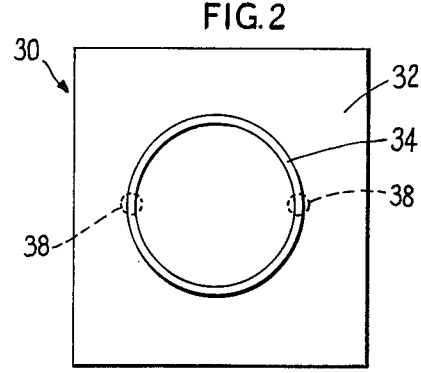
FIG. 2 shows a plan view of an alternative probe.
Figure 3:
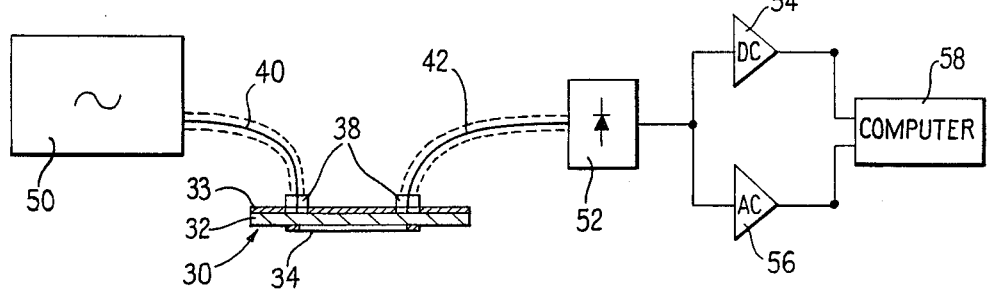
FIG. 3 shows a block diagram of an electric circuit incorporating the probe of FIG. 2, the probe being shown in section.

Referring to FIG. 2 (and FIG. 3), an alternative probe 30, similar in many respects, comprises a thin substrate 32 of polytetrafluoroethylene/glass fibre laminate with a thin layer 33 (not shown in FIG. 2) of copper on its rear surface. On its front surface is a resonant microstrip element 34 in the form of a circular ring-shaped copper strip of mean diameter 33 mm and strip-width 1 mm. Two coaxial cable connectors 38 are mounted in corresponding small circular holes defined in the layer 33 underneath diametrically opposed points on the element 34, and are soldered to the layer 33. As shown in FIG. 3, copper-sheathed coaxial cables 40 and 42 can be inserted into the connectors 38; the layer 33 is then earthed through the sheaths of the cables 40 and 42, while the centre conductors of the connectors 38 abut the rear surface of the substrate 32, the coupling capacitance between the centre conductor and the element 34 being about 20 fF with the consequences discussed above.

In use, the probe 10 or 30 is placed such that a material under test is adjacent to the front surface of the substrate 12 or 32 and hence to the resonant element 14 or 34, and microwaves are capacitively coupled into the element 14 or 34 from a source via the cable 40. The amplitude of the forced microwave oscillations in the element 14 or 34 determines the amplitude of the microwave signal coupled into the output cable 42. In general this forced oscillation will be of small amplitude, but for frequencies which correspond to the fundamental resonant frequency of the element 14 or 34 or to a harmonic of it the oscillation is of large amplitude. The resonant frequencies are those at which the length of the element 14 is an integral number of half wavelengths, or the circumference of the element 34 is an integral number of wavelengths, and this clearly depends upon the velocity of propagation of microwaves along the element 14 or 34. Part of the electromagnetic fields due to microwaves in the element 14 or 34 extends into the material under test, so the material will affect these resonances: the resonant frequency will be determined by the dielectric constant (relative permittivity) of the material under test (because this determines the propagation velocity of the microwaves), and the sharpness of the response (Q) and the peak response will be primarily determined by the dielectric loss of the material. It will be appreciated that because coupling to and from the element 34 in the probe 30 takes place through the substrate 32, the material under test will not affect the coupling.

Figure 4:
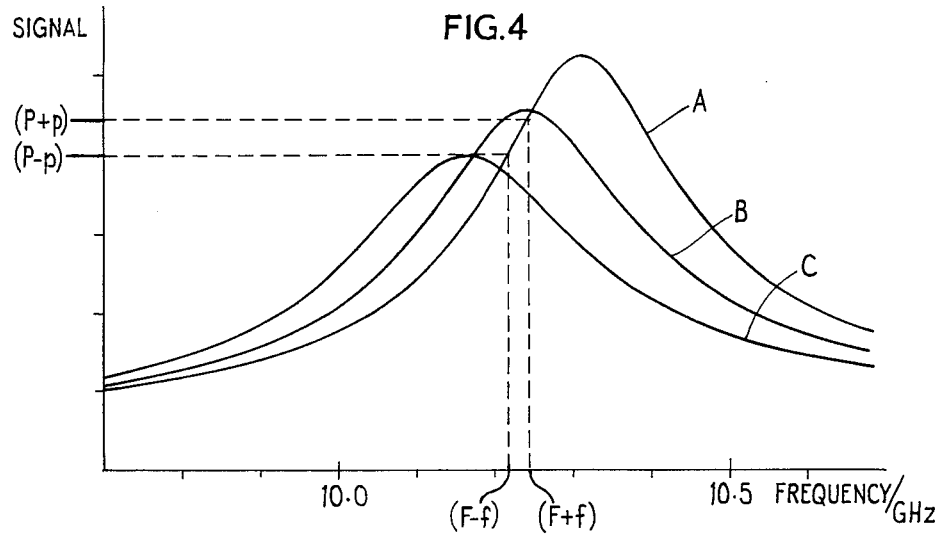
FIG. 4 shows graphically the variation of transmitted microwave signal with frequency with the probe of FIG. 2.

Referring to FIG. 4 there is shown graphically the variation in microwave signal in the output cable 42, for a fixed amplitude of input signal, which would occur if the microwave frequency were to be varied between 9.7 GHz and 10.7 GHz. Three graphs are shown, corresponding to three different materials adjacent to the probe 30: oil with 17% water (graph A), 18% water (graph B), and 19% water (graph C). These graphs show the fifth harmonic resonance. It will be observed that as the water content of the oil increases, the resonant frequency and the Q-value decrease, because the dielectric constant and the dielectric loss both increase. It will be appreciated however that, in performing the method of the invention, complete resonant peaks as shown in FIG. 4 are not observed.

Referring in particular to graph A, if the microwave frequency were to be modulated about a mean frequency F between the two frequencies (F−f) and (F+f) marked by the broken lines, the output signal will have a mean amplitude P (equal to the response at the mean frequency F) and will be modulated between the values (P−p) and (P+p). The amplitude of the modulation, p, is clearly a measure of the gradient of the graph A at the frequency F; the gradient is actually given by (p/f).

Referring now to FIG. 3 there is shown an electrical circuit with which the method of the invention may be performed. The probe 30 is connected by the input cable 40 to a frequency-modulated microwave oscillator 50, and by the output cable 42 to a detector 52. Signals from the detector 52 are passed both to a dc amplifier 54 whose output indicates the mean value of the microwave signal, and also to an ac amplifier 56 whose output indicates the amplitude of the modulation of the microwave signal and so represents the gradient of the signal/frequency graph. From the two outputs from the amplifiers 54 and 56 the dielectric constant and the dielectric loss of the material adjacent to the probe 30 can be determined, and hence the material identified; this may be achieved by a computer 58 programmed with a suitable look-up table, calculated for a particular probe and for a particular mean frequency.

Figure 5:
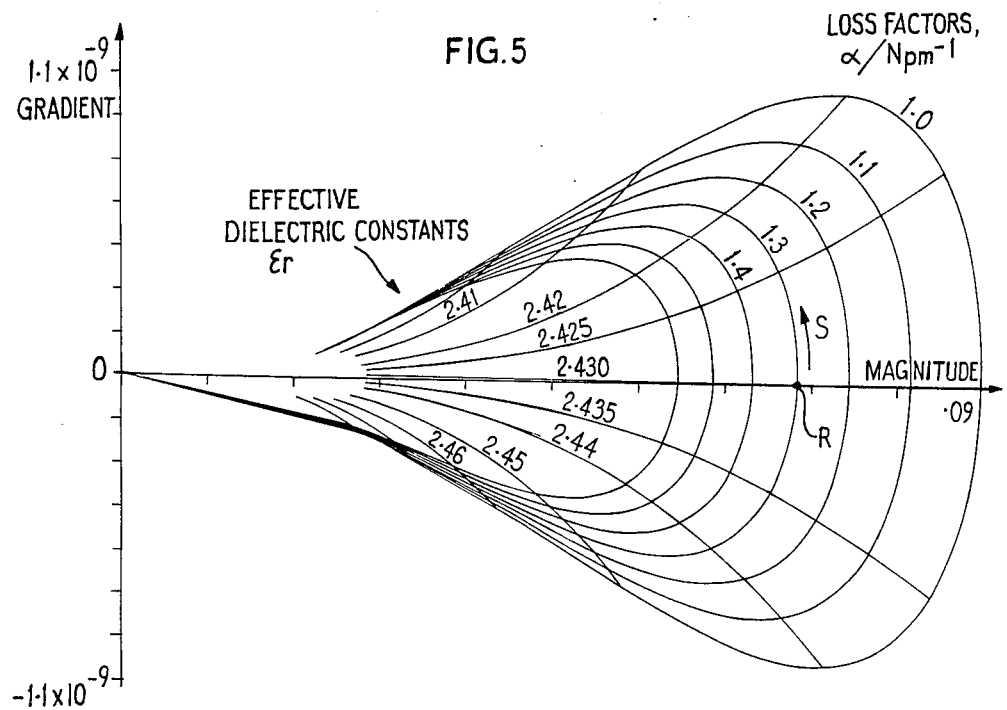
FIG. 5 shows graphically, as a parametric plot, how measurements made with the circuit of FIG. 3 may be used to determine electrical properties of a material.

Referring to FIG. 5, this represents graphically, as a parametric plot, calculated for the probe 30 at a mean frequency of 11.085 GHz, the variation of microwave signal amplitude and gradient with effective dielectric constant of the materials adjacent to the probe, and with the loss factor for the probe. The effective dielectric constant is determined by the dielectric constants of the substrate material and of the material under test, while the loss factor of the probe depends principally upon the dielectric loss of the material under test. For fixed dielectric loss, changing the dielectric constant changes primarily the resonant frequency, so displacing the signal/frequency graph (whose shape is similar to those shown in FIG. 4) along the frequency axis. For example if the effective dielectric constant is initially 2.43 then there is a resonance at 11.085 GHz, and so maximum amplitude and zero gradient (see point R); decreasing the effective dielectric constant causes the amplitude to decrease, while the gradient initially increases rapidly, and then slowly decreases (see arrow S). For fixed dielectric constant, on the other hand, increasing the dielectric loss and so the loss factor of the probe causes decreases in both amplitude and gradient, except when starting at a resonance in which case the gradient remains zero.

Thus, using the circuit of FIG. 3 the mean signal and the gradient of the signal/frequency graph can be measured, and then by means of a look-up table equivalent to FIG. 5, the dielectric loss and the dielectric constant of the material under test can be determined.

In a modification of the circuit of FIG. 3 the oscillator 50 is instead one which can be switched between two discrete frequencies (differing by about 10 MHz), and no ac amplifier 56 is provided. The computer 58 determines the responses at the two discrete frequencies, and calculates their mean, and the difference between them. From this difference the gradient of the signal/frequency graph can readily be determined. The oscillator 50 might be controlled by signals from the computer 58, for example to switch to the other frequency when the computer has determined the response at a first frequency. The modulation is thus effectively a square-wave or a rectangular wave variation in the microwave frequency.

Figure 6:
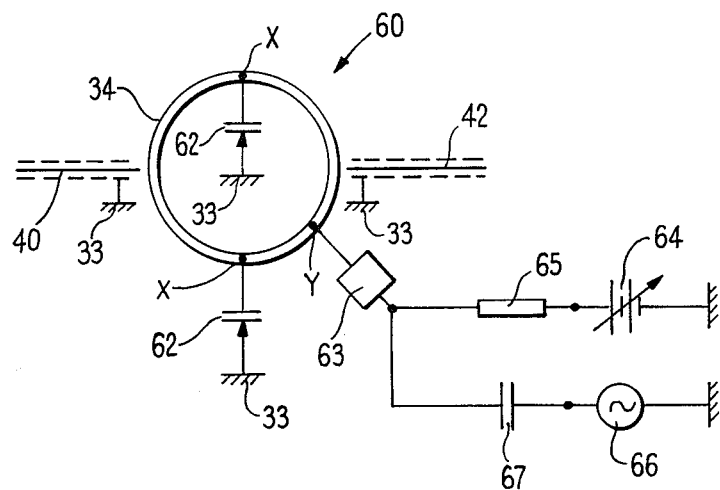
FIG. 6 shows a circuit diagram of a modified version of the probe of FIG. 2 to FIG. 1, this shows a probe 10 of FIG. 2.

Instead of modulating the microwave frequency, as described above, an equivalent result can be achieved instead by modulating the electrical parameters of the resonant element. For example, referring to FIG. 6 there is shown the electric circuit of a modification to the probe of FIGS. 2 and 3, identical features being referred to by the same reference numbers. The probe 60 includes as the resonant element a 33 mm diameter resonant microstrip ring 34 separated by a substrate sheet from an earthed layer of copper 33; input and output coaxial cables 40 and 42 are capacitively coupled to diametrically opposite points on the ring 34 as described previously. At the two points X midway between the input and the output are connected two varactor diodes 62 (i.e. reverse biased diodes whose capacitance is voltage-dependent), each being mounted on the rear of the probe 60 and connected between the ring 34 and the earthed layer 33. At a point Y midway between the output and one point X are connected to the ring 34, via a low-pass filter network 63, a source 64 to provide a dc bias voltage through a resistor 65, and an ac source 66 to provide a modulating voltage through a capacitor 67.

If a bias voltage is applied to the ring 34 by the source 64 it changes the capacitance of the varactors 62. This leads to a change in the resonant frequency of the ring but has little effect on the size and Q-factor of the response. The probe 60 is preferably operated with a microwave frequency near to an even harmonic, as this ensures there is an antinode of electric field at the points X (maximising the effect of the varactors 62).

In operation, the probe 60 is used in a circuit as in FIG. 3 except that the frequency modulated source 50 is replaced by a constant frequency microwave source. The bias voltage is adjusted (e.g. up to 30 V) to ensure that the chosen resonant frequency of the ring 34 is near the frequency of the microwaves. An ac modulating voltage is then applied by the source 66, modulating the capacitance of the varactors 62 and hence the resonant frequency of the ring 34. The signal in the cable 42 is consequently modulated, its ac component being indicative of the gradient of the signal/frequency graph. Thus the dielectric constant and the dielectric loss of the material adjacent to the probe 60 can be determined in the same manner as described above.

We claim:

1. A method for characterising a material, the method using an element in which microwaves can propagate and can resonate, the method comprising arranging the material in such a position relative to the element that at least a part of the electromagnetic fields due to microwaves propagating in the element extend into the material, coupling microwaves into the element at a frequency near to a resonant frequency, sensing the microwave response of the element, both the coupling means and the sensing means being coupled to the element sufficiently weakly to have negligible effect on its natural resonance, and applying a modulating signal so as to modulate the response by substantially less than the peak response of the resonance, hence obtaining a first signal indicative of the mean response, and a second signal indicative of the rate of change of the response with frequency, and using the first and the second signals to characterise the material.

2. A method as claimed in claim 1 wherein the element is an isolated resonant microstrip component, and the material is arranged adjacent to the microstrip component.

3. A method as claimed in claim 1 wherein the element is a resonant chamber, and the material is arranged within the chamber.

4. A method as claimed in claim 1 wherein the first and the second signals are used to determine both the dielectric constant and the dielectric loss of the material.

5. A method as claimed in claim 1 wherein the modulating signal is used to modulate the frequency of the microwaves.

6. A method as claimed in claim 1 wherein the modulating signal is used to modulate the natural resonant frequency of the element.

7. A method as claimed in claim 6 wherein the modulating signal is applied to a voltage-dependent capacitor arranged so as to modulate the natural resonant frequency of the element.

8. A material-characterising apparatus comprising an element in which microwaves can propagate and can resonate, the element in use being arranged in such a position relative to a material to be characterised that at least a part of the electromagnetic fields due to microwaves propagating in the element extend into the material, means for coupling microwaves into the element at a frequency near to a resonant frequency and means for sensing the microwave response of the element, both the coupling means and the sensing means being coupled to the element sufficiently weakly to have a negligible effect on its natural resonance, means for applying a modulating signal so as to modulate the response by substantially less than the peak response of the resonance, means for obtaining a first signal indicative of the mean response, and a second signal indicative of the rate of change of response with frequency, and means responsive to the first and the second signals to characterise the material.

9. An apparatus as claimed in claim 8 wherein the element is an isolated resonant microstrip component.

10. An apparatus as claimed in claim 8 wherein the element is a resonant chamber, within which the material is arranged in use.

11. An apparatus as claimed in claim 8, also comprising means for modulating the natural resonant frequency of the element.

12. An apparatus as claimed in claim 11 wherein the modulating means incorporates a voltage-dependent capacitor connected to the element.

* * * * *